United States Patent
Eschbach et al.

(10) Patent No.: US 12,185,948 B2
(45) Date of Patent: Jan. 7, 2025

(54) POWERED SURGICAL DEVICES INCLUDING STRAIN GAUGES INCORPORATED INTO FLEX CIRCUITS

(71) Applicant: Covidien LP, Mansfield, MA (US)

(72) Inventors: Matthew Eschbach, Cheshire, CT (US); David Nicholas, Trumbull, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/460,857

(22) Filed: Sep. 5, 2023

(65) Prior Publication Data

US 2023/0404580 A1    Dec. 21, 2023

Related U.S. Application Data

(63) Continuation of application No. 17/734,494, filed on May 2, 2022, now Pat. No. 11,751,874, which is a
(Continued)

(51) Int. Cl.
| | | |
|---|---|---|
| *A61B 17/072* | (2006.01) | |
| *A61B 17/00* | (2006.01) | |
| *A61B 17/29* | (2006.01) | |

(52) U.S. Cl.
CPC ............ *A61B 17/07207* (2013.01); *A61B 2017/00022* (2013.01); *A61B 2017/00734* (2013.01);
(Continued)

(58) Field of Classification Search
CPC ............ A61B 17/07207; A61B 17/068; A61B 17/072; A61B 2090/065; A61B 90/06;
(Continued)

(56) References Cited

U.S. PATENT DOCUMENTS

| | | |
|---|---|---|
| 2,957,353 A | 10/1960 | Babacz |
| 3,111,328 A | 11/1963 | Di Rito et al. |

(Continued)

FOREIGN PATENT DOCUMENTS

| | | |
|---|---|---|
| CA | 2451558 A1 | 1/2003 |
| CN | 1547454 A | 11/2004 |

(Continued)

OTHER PUBLICATIONS

Japanese Notice of Allowance issued in Japanese Application No. 2019-107867 dated Nov. 14, 2023 (5 pages).
(Continued)

*Primary Examiner* — Veronica Martin

(57) ABSTRACT

A surgical device includes an end effector and a handle assembly operably coupled to the end effector. The end effector includes an anvil assembly and a cartridge assembly pivotally coupled to one another. The cartridge assembly includes a staple cartridge, a cartridge carrier, and a strain gauge. The cartridge carrier includes an elongated support channel configured to receive the staple cartridge, the elongated support channel defined by an inner first surface and a pair of inner second surfaces. The inner first surface includes a recess defined therein, and the strain gauge is disposed within the recess. The handle assembly includes a power-pack configured to receive sensor data from the strain gauge of the end effector and to control a function of the end effector in response to the sensor data.

20 Claims, 11 Drawing Sheets

Related U.S. Application Data continuation of application No. 16/413,919, filed on May 16, 2019, now abandoned.

(60) Provisional application No. 62/687,846, filed on Jun. 21, 2018.

(52) U.S. Cl.
CPC ........... *A61B 2017/07257* (2013.01); *A61B 2017/07271* (2013.01); *A61B 2017/2925* (2013.01); *A61B 2017/2927* (2013.01); *A61B 2562/0261* (2013.01)

(58) Field of Classification Search
CPC .......... A61B 2017/00022; A61B 17/29; A61B 2017/00398; A61B 2017/07271; A61B 2090/061; A61B 2090/064; A61B 2017/00119; A61B 2090/0811; A61B 2017/07214; A61B 2017/07285
See application file for complete search history.

(56) References Cited

U.S. PATENT DOCUMENTS

| | | |
|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | Mckean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |

(56) References Cited

U.S. PATENT DOCUMENTS

| | | |
|---|---|---|
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |

(56) References Cited

U.S. PATENT DOCUMENTS

| | | |
|---|---|---|
| 9,282,963 B2 | 3/2016 | Bryant |
| 9,295,522 B2 | 3/2016 | Kostrzewski |
| 9,307,986 B2 | 4/2016 | Hall et al. |
| 11,751,874 B2 | 9/2023 | Eschbach et al. |
| 2001/0031975 A1 | 10/2001 | Whitman |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0105478 A1 | 6/2003 | Whitman et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0273135 A1 | 12/2006 | Beetel |
| 2006/0278680 A1 | 12/2006 | Viola |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton, IV et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0012556 A1 | 1/2009 | Boudreaux et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0198220 A1 | 8/2010 | Boudreaux et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Kia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0228358 A1 | 9/2012 | Zemlok et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0200612 A1 | 7/2014 | Weir et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |

(56) References Cited

U.S. PATENT DOCUMENTS

| | | |
|---|---|---|
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera |
| 2016/0113648 A1 | 4/2016 | Zergiebel et al. |
| 2016/0113649 A1 | 4/2016 | Zergiebel et al. |
| 2016/0249921 A1 | 9/2016 | Cappola et al. |
| 2016/0256184 A1 | 9/2016 | Shelton, IV et al. |
| 2016/0296234 A1 | 10/2016 | Richard |
| 2016/0310134 A1 | 10/2016 | Contini et al. |
| 2017/0030784 A1 | 2/2017 | Mason et al. |
| 2017/0296183 A1 | 10/2017 | Shelton, IV et al. |
| 2018/0049821 A1* | 2/2018 | Shelton, IV ... A61B 17/320068 |
| 2019/0000535 A1* | 1/2019 | Messerly ............... A61B 17/29 |

FOREIGN PATENT DOCUMENTS

| | | |
|---|---|---|
| CN | 1957854 A | 5/2007 |
| CN | 101495046 A | 7/2009 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1728475 A2 | 12/2006 |
| EP | 1769754 A1 | 4/2007 |
| EP | 2316345 A1 | 5/2011 |
| EP | 2668910 A2 | 12/2013 |
| ES | 2333509 A1 | 2/2010 |
| JP | 2-45406 | 3/1990 |
| JP | 2005125075 A | 5/2005 |
| JP | 2006334417 A | 12/2006 |
| JP | 2008272457 A | 11/2008 |
| JP | 2011036656 A | 2/2011 |
| JP | 2017531535 A | 10/2017 |
| JP | 2017532168 A | 11/2017 |
| KR | 20120022521 A | 3/2012 |
| WO | 2011108840 A2 | 9/2011 |
| WO | 2012040984 A1 | 4/2012 |

OTHER PUBLICATIONS

Extended European Search Report corresponding to International Application No. EP 14 18 4882.0 dated May 12, 2015.
Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.5-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Partial European Search Report dated Nov. 27, 2019 corresponding to counterpart Patent Application EP 19181510.9.
Extended European Search Report dated Apr. 6, 2020 corresponding to counterpart Patent Application EP 19181510.9.
Chinese Office Action issued in corresponding Chinese Application No. 201910521303.0 dated Apr. 11, 2023, 13 pages.
Japanese Office Action issued in Japanese Patent Application No. 2019-107867 dated Jun. 8, 2023, 11 pages.

* cited by examiner

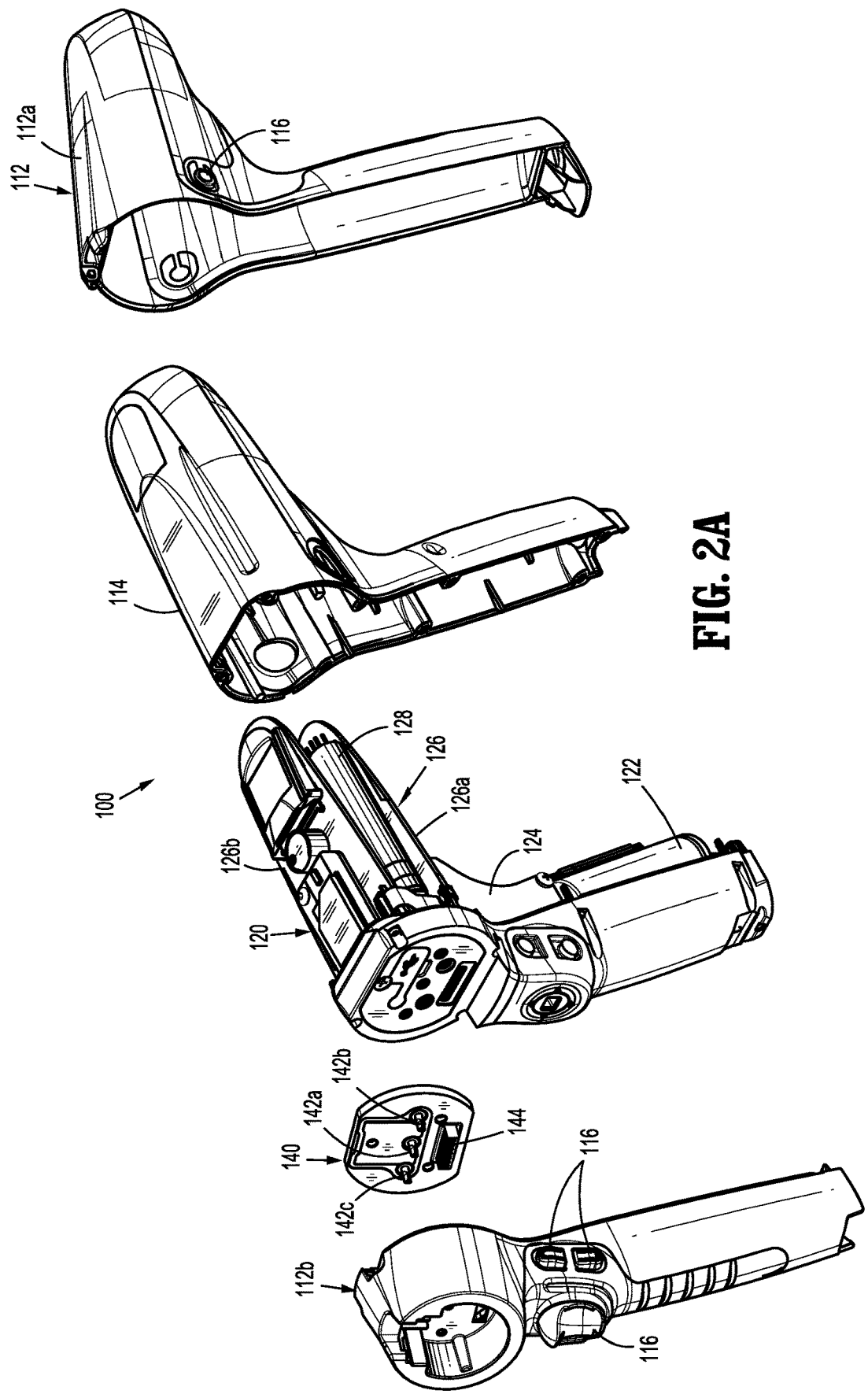

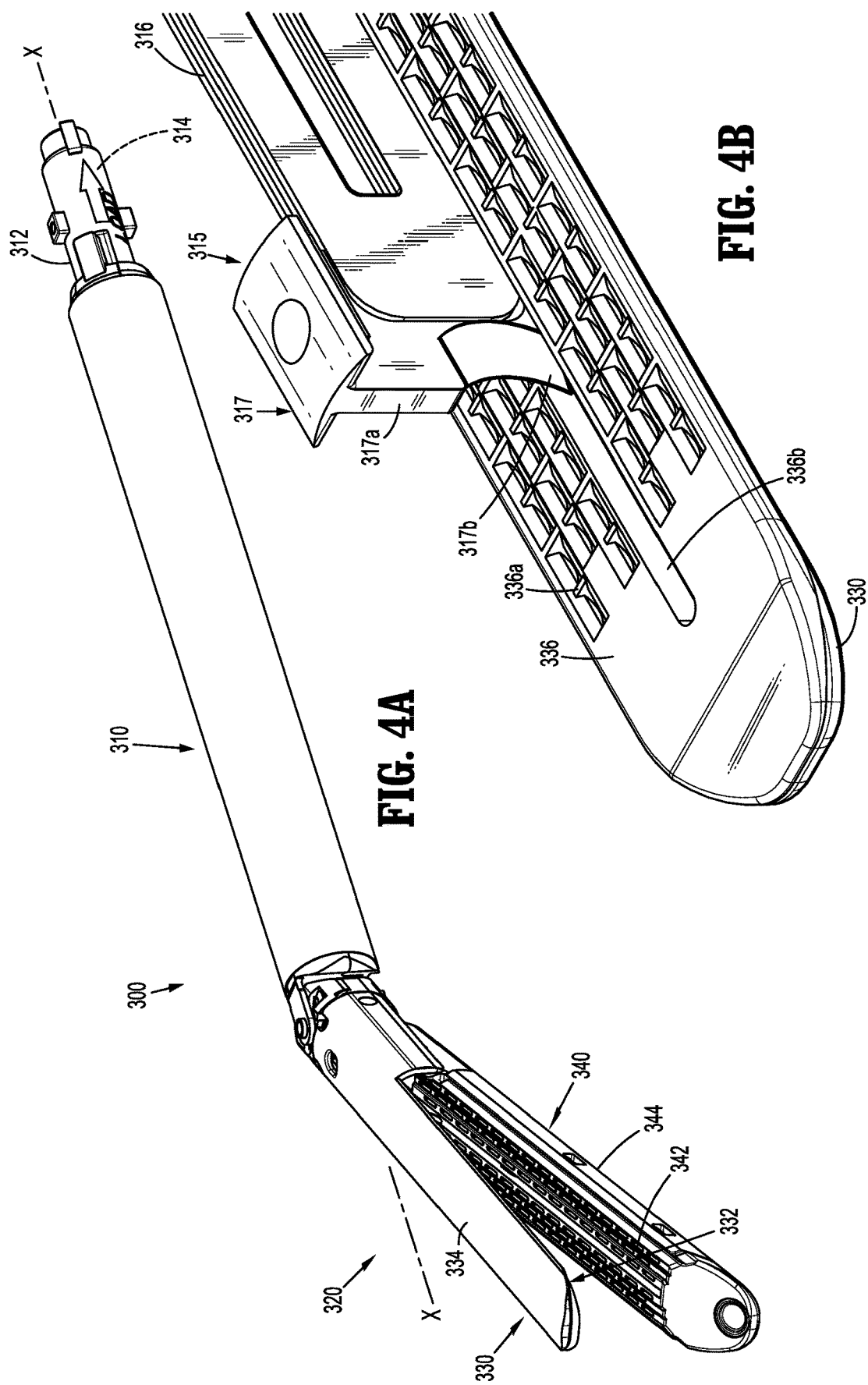

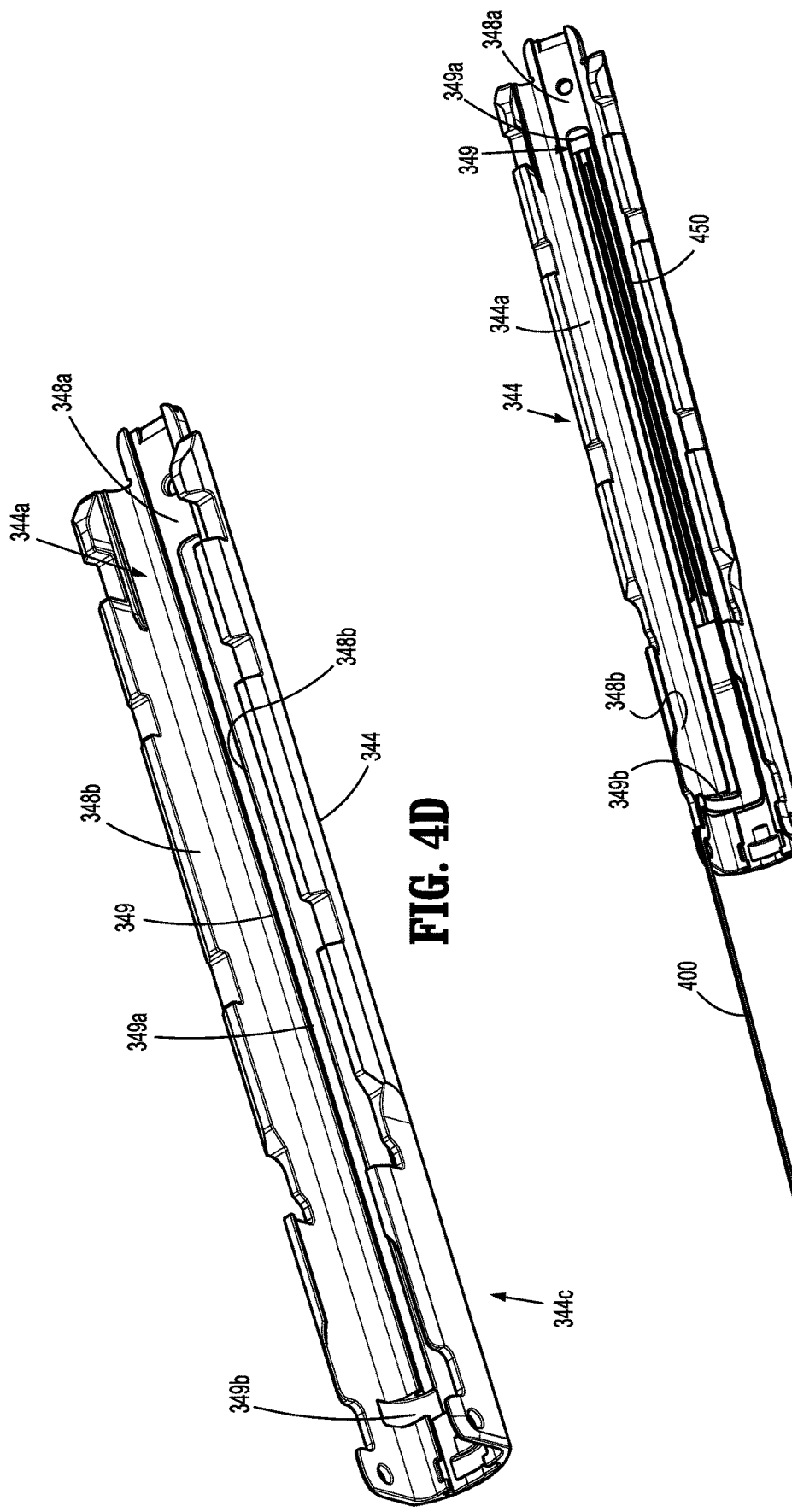

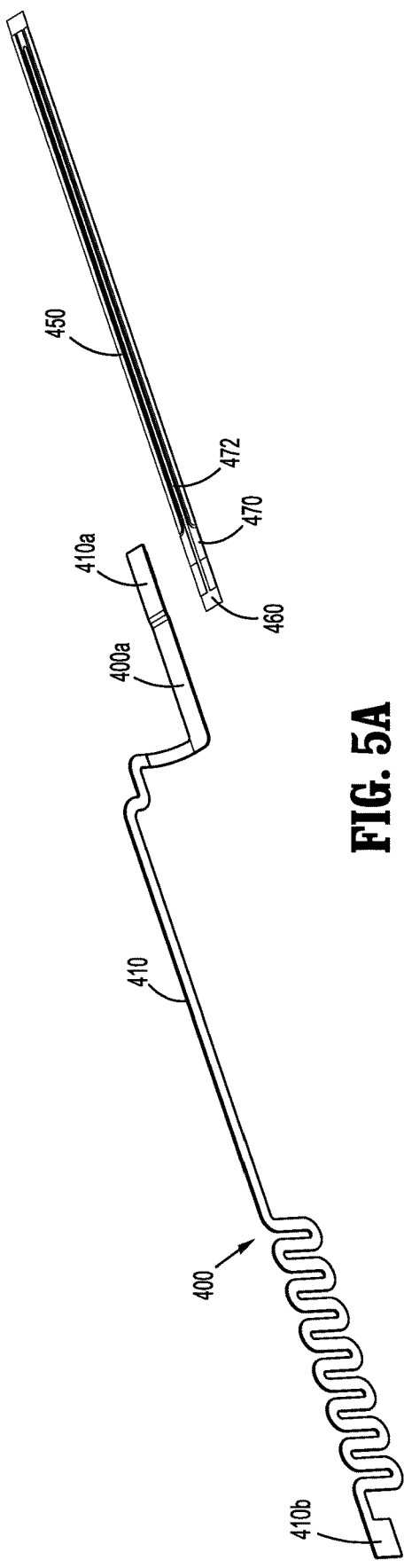
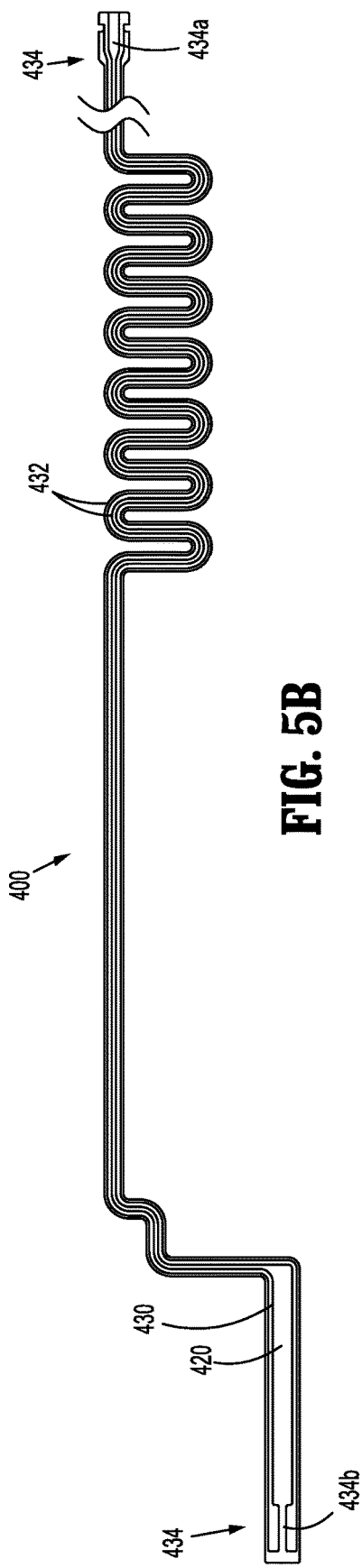
FIG. 5A
FIG. 5B

POWERED SURGICAL DEVICES INCLUDING STRAIN GAUGES INCORPORATED INTO FLEX CIRCUITS

CROSS-REFERENCE TO RELATED APPLICATIONS

This application is a continuation application which claims the benefit of and priority to U.S. patent application Ser. No. 17/734,494, filed May 2, 2022, which is a continuation application claiming the benefit of and priority to U.S. patent application Ser. No. 16/413,919, filed May 16, 2019, which claims the benefit of and priority to U.S. Provisional Patent Application No. 62/687,846, filed Jun. 21, 2018, the entire disclosure of each of which being incorporated by reference herein.

TECHNICAL FIELD

The present disclosure relates generally to surgical devices. More particularly, the present disclosure relates to powered handheld electromechanical instruments including strain gauges.

BACKGROUND

A number of surgical device manufacturers have developed product lines with proprietary powered drive systems for operating and/or manipulating surgical devices. In many instances the surgical devices include a powered handle assembly, which is reusable, and a disposable end effector or the like that is selectively connected to the powered handle assembly prior to use and then disconnected therefrom following use in order to be disposed of or, in some instances, sterilized for re-use.

Sensors may be used to enhance control of functions in powered surgical devices, such as surgical stapling devices. For example, some powered surgical stapling devices use current sensors to detect electrical current draw from a motor of the device, or load reading sensors along a drive assembly of the device, as an indicator of the forces required to compress tissue, to form staples, and/or to transect the tissue. Load reading sensors can be used to detect pre-set loads and cause the powered surgical stapling device to react thereto. For example, during clamping of thick tissue, the load will rise to a pre-determined limit where the device can slow clamping to maintain the clamping force as the tissue relaxes. This allows for clamping of thick tissue without damage to such tissue (e.g., serosa tears). Data collected from these sensors may also be used to control the speed of firing, which has been shown to improve staple formation by slowing the stapler speed and lowering the firing force. The data may also be used in other aspects of the stapling process, such as detecting end stop and emergency stopping to prevent damage to the end effector.

It would be desirable to reduce or minimize the cost of assembling sensors, such as strain gauges, into powered surgical devices and, in particular, into disposable powered surgical devices or disposable components of such devices (e.g., an end effector), by, for example, simplifying the assembly process and/or minimizing the total number of components and/or connections required for assembly.

SUMMARY

A surgical device in accordance with aspects of the present disclosure includes an end effector and a handle assembly operably coupled to the end effector. The end effector includes an anvil assembly and a cartridge assembly pivotally coupled to one another. The cartridge assembly includes a staple cartridge, a cartridge carrier, and a strain gauge. The cartridge carrier includes an elongated support channel configured to receive the staple cartridge, the elongated support channel defined by an inner first surface and a pair of inner second surfaces. The inner first surface includes a recess defined therein, and the strain gauge is disposed within the recess of the cartridge carrier. The handle assembly includes a power-pack configured to receive sensor data from the strain gauge of the end effector and to control a function of the end effector in response to the sensor data.

The recess of the cartridge carrier may include a first portion extending longitudinally along a majority of the length of the cartridge carrier. The strain gauge may be secured to the first portion of the recess. The recess of the cartridge carrier may include a second portion extending from the first portion at an angular orientation relative thereto and open to one of the pair of inner second surfaces of the cartridge carrier. A flex circuit may be disposed within the second portion of the cartridge carrier and extend distally along the respective one of the pair of inner second surface of the cartridge carrier.

The strain gauge may be embedded within the flex circuit. The flex circuit may include a first region including resistor traces forming the strain gauge, and a second region including conductive traces coupled to the strain gauge. The flex circuit may include a first dielectric layer, a resistive layer disposed over the first dielectric layer, a conductive layer disposed over the resistive layer. The resistive layer may extend an entire length of the first dielectric layer. The resistive layer may include resistor traces patterned in a first region of the flex circuit and a continuous plane of resistive material in a second region of the flex circuit. The conductive layer may be disposed over the resistive layer with the resistor traces masked from the conductive layer.

The end effector may further include a microcontroller coupled to a memory. The microcontroller may be electrically coupled to the strain gauge and configured to receive sensor data from the strain gauge, and the memory may be configured to store the sensor data.

An end effector in accordance with aspects of the present disclosure includes an anvil assembly and a cartridge assembly pivotally coupled to one another. The cartridge assembly includes a staple cartridge, a cartridge carrier, and a strain gauge. The cartridge carrier includes an elongated support channel configured to receive the staple cartridge, the elongated support channel defined by an inner first surface and a pair of inner second surfaces. The inner first surface includes a recess defined therein, and the strain gauge is disposed within the recess of the cartridge carrier.

The recess of the cartridge carrier may include a first portion extending longitudinally along a majority of the length of the cartridge carrier. The strain gauge may be secured to the first portion of the recess. The recess of the cartridge carrier may include a second portion extending from the first portion at an angular orientation relative thereto and open to one of the pair of inner second surfaces of the cartridge carrier. A flex circuit may be disposed within the second portion of the cartridge carrier and extend distally along the respective one of the pair of inner second surfaces of the cartridge carrier.

The strain gauge may be embedded within the flex circuit. The flex circuit may include a first region including resistor traces forming the strain gauge, and a second region including conductive traces coupled to the strain gauge. The flex circuit may include a first dielectric layer, a resistive layer disposed over the first dielectric layer, a conductive layer disposed over the resistive layer. The resistive layer may extend an entire length of the first dielectric layer. The resistive layer may include resistor traces patterned in a first region of the flex circuit and a continuous plane of resistive material in a second region of the flex circuit. The conductive layer may be disposed over the resistive layer with the resistor traces masked from the conductive layer.

The end effector may further include a microcontroller coupled to a memory. The microcontroller may be electrically coupled to the strain gauge and configured to receive sensor data from the strain gauge, and the memory may be configured to store the sensor data.

BRIEF DESCRIPTION OF THE DRAWINGS

Embodiments of the present disclosure are described herein with reference to the accompanying drawings, wherein:

FIG. 2A is a perspective view, with parts separated, of the handle housing of the surgical device of FIG. 1;

FIG. 4A is a perspective view of the end effector of the surgical device of FIG. 1;

FIG. 4B is a perspective view of an anvil assembly and a drive assembly of the end effector of FIG. 4A;

FIG. 4D is a perspective view of a cartridge carrier of the end effector of FIG. 4C;

FIG. 4E is a top view of the cartridge carrier of FIG. 4D including a flex circuit and a strain gauge secured thereto in accordance with an embodiment of the present disclosure;

FIG. 5A is a perspective view of the strain gauge and the flex circuit of FIG. 4E;

FIG. 5B is a top view of the flex circuit of FIG. 5A;

DETAILED DESCRIPTION OF EMBODIMENTS

Figure 1:
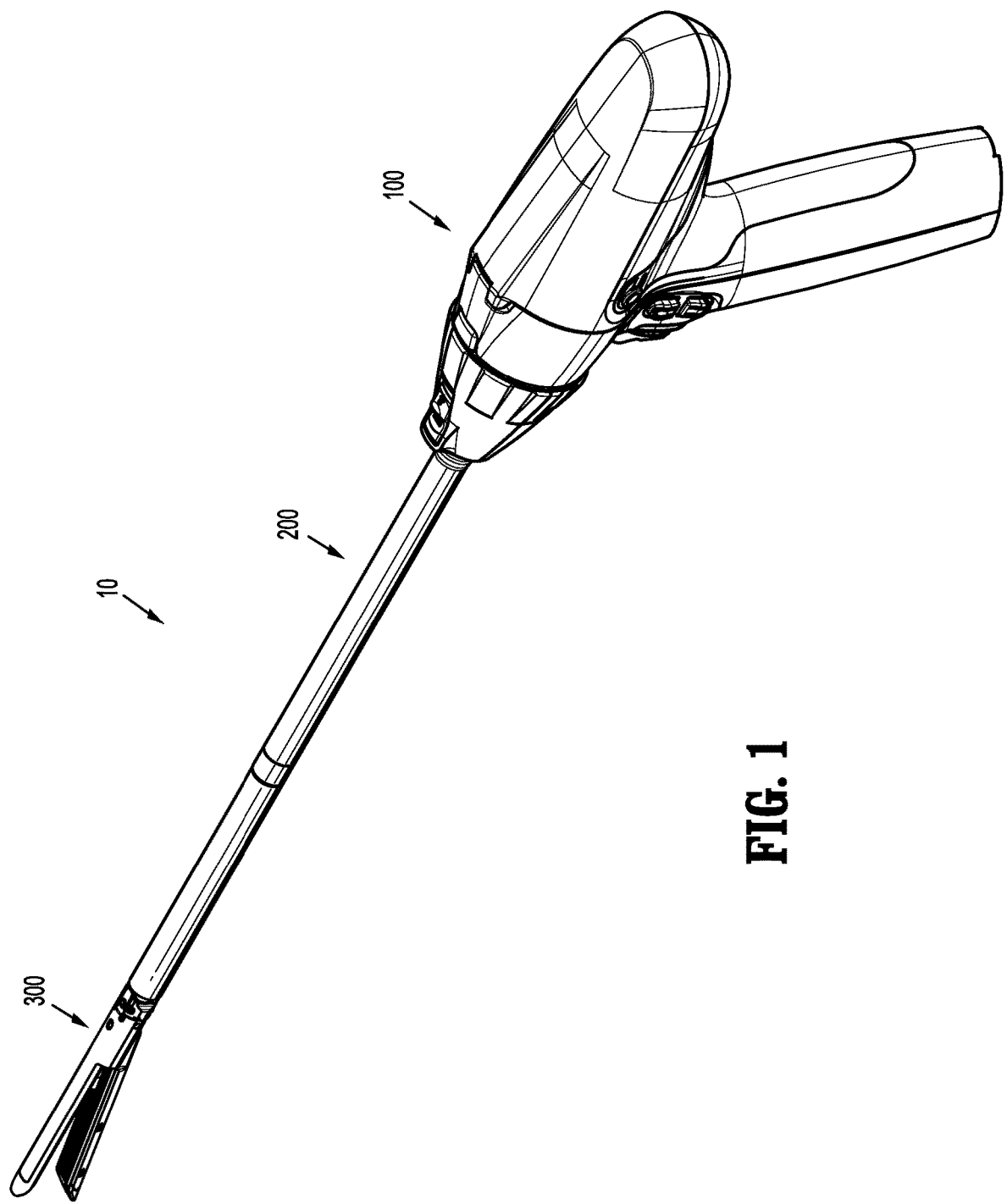
FIG. 1 is a perspective view of a surgical device including a handle housing, an adapter assembly, and an end effector in accordance with an embodiment of the present disclosure.

Embodiments of the present disclosure are now described in detail with reference to the drawings in which like reference numerals designate identical or corresponding elements in each of the several views. Throughout this description, the term "proximal" refers to a portion of a device, or component thereof, that is closer to a user, and the term "distal" refers to a portion of the device, or component thereof, that is farther from the user.

Turning now to FIG. 1, a surgical device 10, in accordance with an embodiment of the present disclosure, is in the form of a powered handheld electromechanical instrument. The surgical device 10 includes a handle assembly 100, an adapter assembly 200, and a tool assembly or end effector 300. The handle assembly 100 is configured for selective connection with the adapter assembly 200 and, in turn, the adapter assembly 200 is configured for selective connection with the end effector 300.

The handle assembly 100, the adapter assembly 200, and the end effector 300 will only further be described to the extent necessary to disclose aspects of the present disclosure. For a detailed description of the structure and function of exemplary handle and adapter assemblies, and end effectors, reference may be made to commonly owned U.S. Patent Appl. Pub. No. 2016/0310134 ("the '134 Publication"), the entire content of which is incorporated herein by reference.

With reference now to FIG. 2A, the handle assembly 100 includes an outer housing shell 112, including a proximal half-section 112a and a distal half-section 112b, and an inner handle housing 114 disposed within the outer housing shell 112. The outer housing shell 112 includes a plurality of actuators 116 (e.g., finger-actuated control buttons, knobs, toggles, slides, interfaces, and the like) for activating various functions of the surgical device 10 (FIG. 1), and the inner handle housing 114 houses a power-pack 120 configured to power and control various operations of the surgical device 10.

Figure 2B:
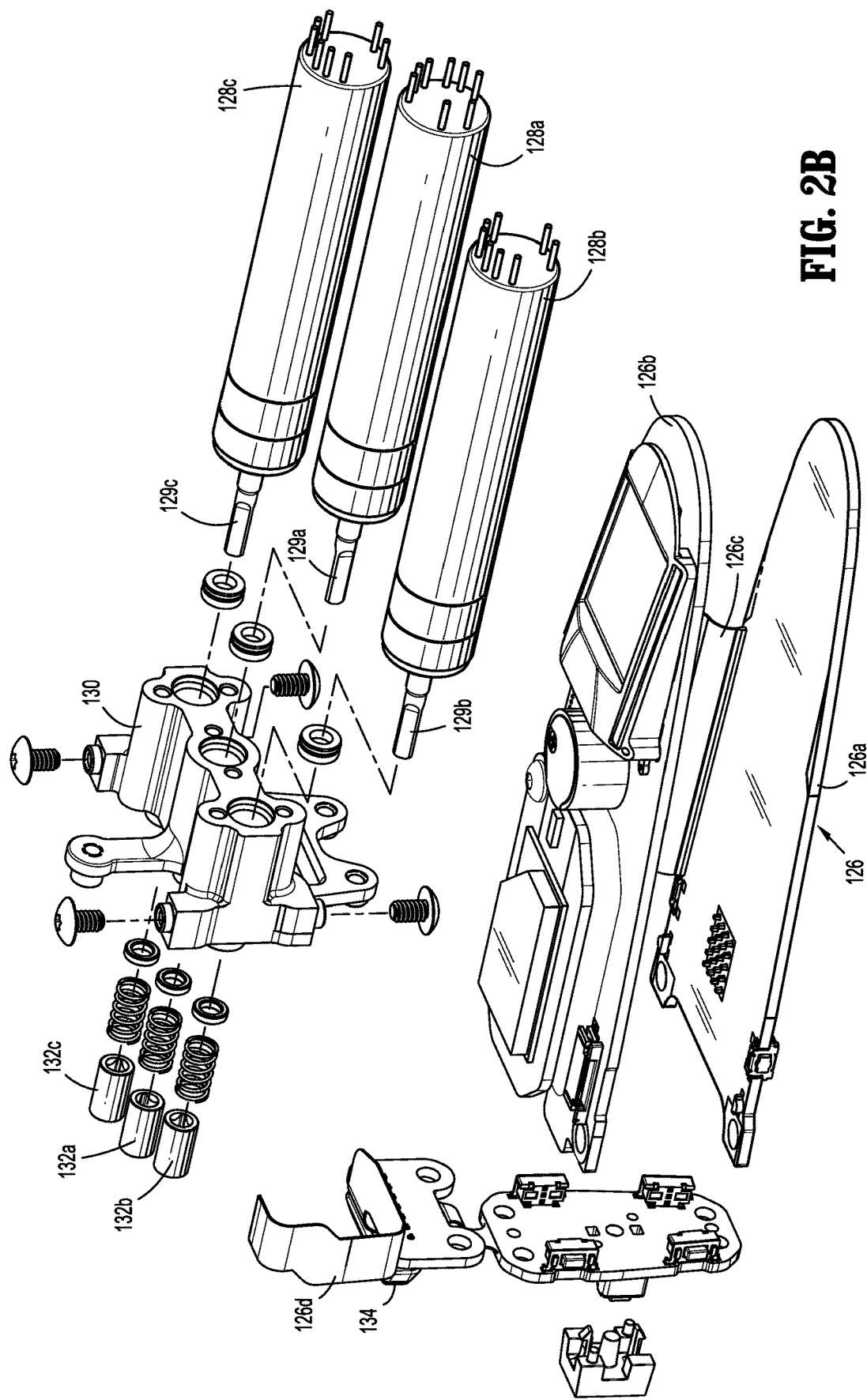
FIG. 2B is a perspective view, with parts separated, of a motor assembly and a control assembly of the handle housing of FIG. 2A.

As shown in FIGS. 2A and 2B, the power-pack 120 includes a rechargeable battery 122 configured to supply power to any of the electrical components of the surgical device 10, a battery circuit board 124, and a controller circuit board 126. The controller circuit board 126 includes a motor controller circuit board 126a, a main controller circuit board 126b, and a first ribbon cable 126c interconnecting the motor controller circuit board 126a and the main controller circuit board 126b. The motor controller circuit board 126a is communicatively coupled with the battery circuit board 124 enabling communication therebetween and between the battery circuit board 124 and the main controller circuit board 126b.

The main controller circuit board 126a includes a 1-wire communication system including three 1-wire buses which enables communication between the power-pack 120 and the battery 122, the power-pack 120 and the adapter assembly 200 (FIG. 1), and the power-pack 120 and the outer shell housing 112. Specifically, with regard to communication between the power-pack 120 and the adapter assembly 200, the 1-wire bus establishes a communication line between a 1-wire master chip of the main controller circuit board 126b and a 1-wire memory chip of a circuit board 224 (FIG. 3B) of the adapter assembly 200. This communication line allows for calibration and communication of data and control signals between the handle assembly 100 and the adapter assembly 200, and enables information stored in the 1-wire memory chip of the circuit board 224 of the adapter assembly 200 to be accessed, updated, and/or incremented by the power-pack 120.

The power-pack 120 further includes motors 128 (e.g., a first motor 128a, a second motor 128b, and a third motor 128c) each electrically connected to the controller circuit board 126 and the battery 122. The motors 128a, 128b, 128c are disposed between the motor controller circuit board 126a and the main controller circuit board 126*b*. Each of the motors 128*a*, 128*b*, 128*c* includes a respective motor shaft 129*a*, 129*b*, 129*c* extending therefrom for transmitting rotative forces or torque.

Each of the motors 128*a*, 128*b*, 128*c* is controlled by a respective motor controller (not shown) disposed on the motor controller circuit board 126*a*, and each motor controller is electrically coupled to a main controller or master chip disposed on the main controller circuit board 126*b* via the first ribbon cable 126*c* which connects the motor controller circuit board 126*a* with the main controller circuit board 126*b*. The master chip is also coupled to memory, which is also disposed on the main controller circuit board 126*b*.

Each of the motor 128*a*, 128*b*, 128*c* is supported on a motor bracket 130 such that the motor shafts 129*a*, 129*b*, 129*c* are rotatably disposed within respective apertures of the motor bracket 130. The motor bracket 130 rotatably supports three rotatable drive connector sleeves 132*a*, 132*b*, 132*c* that are keyed to respective motor shafts 129*a*, 129*b*, 129*c* of the motors 128*a*, 128*b*, 128*c*. The drive connector sleeves 132*a*, 132*b*, 132*c* non-rotatably receive proximal ends of respective coupling shafts 142*a*, 142*b*, 142*c* of a plate assembly 140 of the handle assembly 100, when the power-pack 120 is disposed within the outer shell housing 112.

The motor bracket 130 also supports an electrical adapter interface receptacle 134. The electrical adapter interface receptacle 134 is in electrical connection with the main controller circuit board 126*b* by a second ribbon cable 126*d*. The electrical adapter interface receptacle 134 defines a plurality of electrical slots for receiving respective electrical contacts or blades extending from a pass-through connector 144 of the plate assembly 140 of the handle assembly 100.

Rotation of the motor shafts 129*a*, 129*b*, 129*c* by respective motors 128*a*, 128*b*, 128*c* function to drive shafts and/or gear components of the adapter assembly 200 in order to perform the various operations of the surgical device 10. In particular, the motors 128*a*, 128*b*, 128*c* of the power-pack 120 are configured to drive shafts and/or gear components of the adapter assembly 200 in order to selectively move a tool assembly 320 (FIG. 4A) of the end effector 300 relative to a proximal body portion 310 (FIG. 4A) of the end effector 300, to rotate the end effector 300 about a longitudinal axis "X" (FIG. 4A), to move a cartridge assembly 340 (FIG. 4A) relative to an anvil assembly 330 (FIG. 4A) of the end effector 300, and/or to fire staples from within the cartridge assembly 340 of the end effector 300.

Figure 3A:
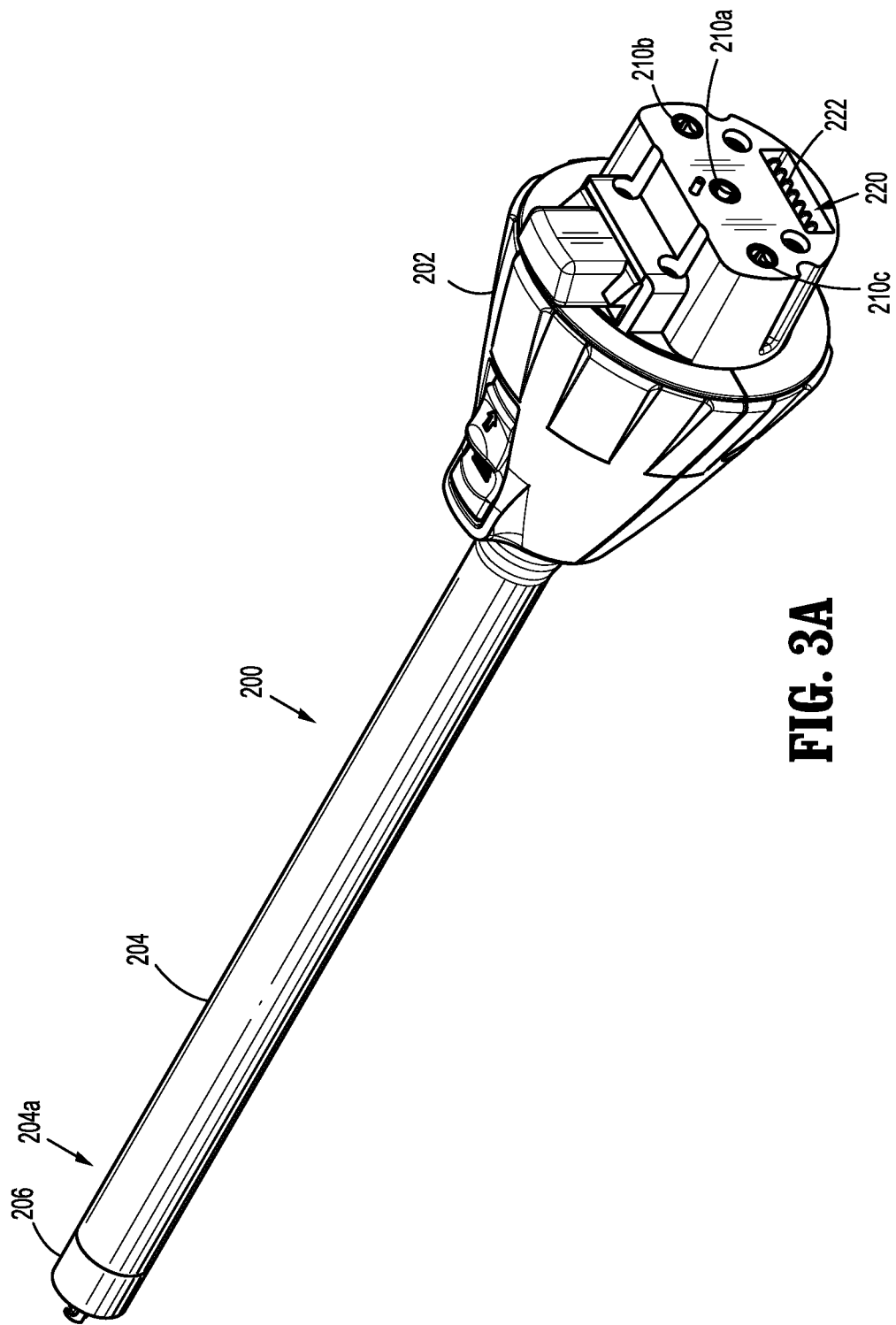
FIG. 3A is a perspective view of the adapter assembly of the surgical device of FIG. 1.

Referring now to FIG. 3A, the adapter assembly 200 includes an outer knob housing or connector housing 202 and an outer tube or sleeve 204 extending distally from the outer knob housing 202 and terminating at a distal cap 206. The outer knob housing 202 is configured for operable connection to the handle assembly 100 (FIG. 1) and the outer tube 204 is configured for operable connection to the end effector 300 (FIG. 1).

Rotatable connector sleeves 210*a*, 210*b*, 210*c* are disposed within the outer knob housing 202 and are configured and adapted to mate, through a keyed and/or substantially non-rotatable interface, with respective coupling shafts 142*a*, 142*b*, 142*c* (FIG. 2A) of the plate assembly 140 of the handle housing 100 such that rotation of each of the coupling shafts 142*a*, 142*b*, 142*c* causes a corresponding rotation of the corresponding connector sleeve 210*a*, 210*b*, 210*c* of the adapter assembly 200. The mating of the coupling shafts 142*a*, 142*b*, 142*c* of the handle assembly 100 with the connector sleeves 210*a*, 210*b*, 210*c* of the adapter assembly 200 allows rotational forces to be independently transmitted via each of the three respective connector interfaces. The coupling shafts 142*a*, 142*b*, 142*c* of the handle assembly 100 are configured to be independently rotated by respective motors 128*a*, 128*b*, 128*c* (FIG. 2B) such that rotational force(s) are selectively transferred from the motor(s) 128*a*, 128*b*, 128*c* of the handle assembly 100 to the adapter assembly 200.

Adapter assembly 200 includes a plurality of force/rotation transmitting/converting assemblies (not shown), each disposed within an inner housing assembly (not shown) of the outer knob housing 202 and the outer tube 204. Each force/rotation transmitting/converting assembly is configured and adapted to transmit/convert a speed/force of rotation (e.g., increase or decrease) of the coupling shafts 142*a*, 142*b*, 142*c* (FIG. 2A) of the handle assembly 100 before transmission of such rotational speed/force to the end effector 300.

Specifically, each force/rotation transmitting/converting assembly is configured and adapted to transmit or convert a rotation of the first, second and third coupling shafts 142*a*, 142*b*, 142*c* of the handle assembly 100 into: axial translation of an articulation bar (not shown) of the adapter assembly 200 to effectuate articulation of the end effector 300 (FIG. 1); a rotation of a ring gear (not shown) of the adapter assembly 200 to effectuate rotation of the adapter assembly 200, and thus, the end effector 300; or axial translation of a distal drive member (not shown) of the adapter assembly 200 to effectuate closing, opening, and firing of the end effector 300.

Figure 3C:
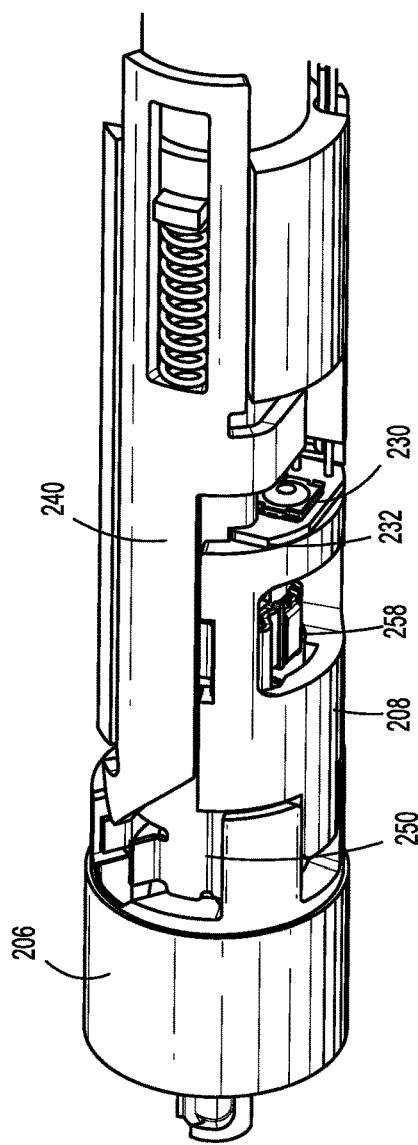
FIG. 3C is a cutaway view of a distal portion of the adapter assembly of FIG. 3A.
Figure 3D:
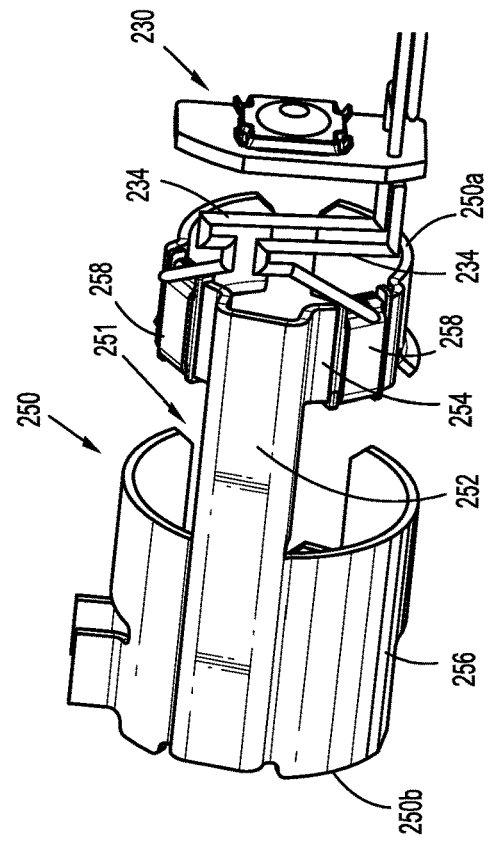
FIG. 3D is a perspective view of an annular member and a switch of the adapter assembly of FIG. 3C.
Figure 3B:
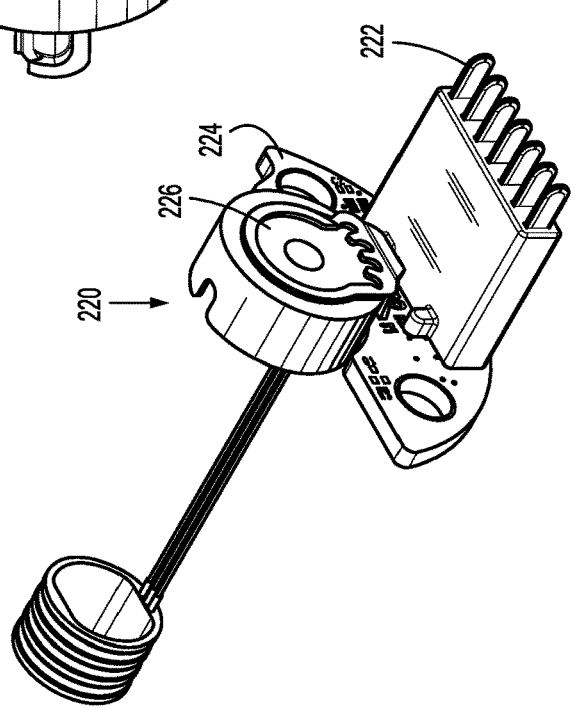
FIG. 3B is a perspective view of an electrical assembly of the adapter assembly of FIG. 3A.

As shown in FIG. 3B, in conjunction with FIG. 3A, an electrical assembly 220 is supported on and in outer knob housing 202. The electrical assembly 220 includes a plurality of electrical contact blades 222 supported on a circuit board 224 for electrical connection to pass-through connector 144 (FIG. 2A) of the plate assembly 140 of the handle assembly 100. The electrical assembly 220 also includes a strain gauge 226 electrically connected to the circuit board 224 for closed-loop feedback of firing/clamping loads exhibited by the adapter assembly 200 and regulated by the power-pack 120 (FIG. 2A), which sets the speed current limit on the appropriate motor 128*a*, 128*b*, 128*c* (FIG. 2B).

The circuit board 224 includes a memory configured to store data relating to the adapter assembly 200 such as unique ID information (electronic serial number); type information; status information; whether an end effector has been detected, identified, and verified; usage count data; and assumed autoclave count data. The electrical assembly 220 serves to allow for calibration and communication of information (e.g., identifying information, life-cycle information, system information, force information) to the main controller circuit board 126*b* (FIG. 2A) of the power-pack 120 via the electrical adapter interface receptacle 134 (FIG. 2B) of the power-pack 120 of the handle assembly 100.

With reference now to FIG. 3C, in conjunction with FIG. 3A, the adapter assembly 200 further includes a switch 230, a sensor link or switch actuator 240, and an annular member 250, each of which is disposed within a distal portion 204*a* of the outer tube 204. The switch 230 is configured to toggle in response to a coupling of the end effector 300 (FIG. 1) to the outer tube 204. The switch 230 is mounted on a printed circuit board 232 that is electrically connected with the controller circuit board 126 (FIG. 2A) of the power-pack 120 of the handle housing 100. The switch 230 is configured to couple to a memory 352 (FIG. 4F) of the end effector 300. The memory 352 of the end effector 300 is configured to store data pertaining to the end effector 300 and is configured to provide the data to the controller circuit board 126 (FIG. 2A) of the handle assembly 100 in response to coupling of the end effector 300 to the outer tube 204. The power-pack 120 monitors communication between the power-pack 120 and the adapter assembly 200 and is able to detect that the end effector 300 is engaged to or disengaged from the distal portion 204a of the outer tube 204 by recognizing that the switch 230 has been toggled.

The switch actuator 240 is slidingly disposed within the distal portion 204a of the outer tube 204. The switch actuator 240 is longitudinally movable between proximal and distal portions, and toggles the switch 230 during movement between the proximal and distal positions.

As shown in FIGS. 3C and 3D, the annular member 250 is rotatably disposed within an inner housing 208 which, in turn, is disposed within the outer tube 204 (FIG. 3A). The annular member 250 extends from a proximal end 250a to a distal end 250b, and defines a cylindrical passageway 251 therethrough configured for disposal of an outer housing 312 (FIG. 4A) of the end effector 300. The annular member 250 includes a longitudinal bar 252 interconnecting a first ring 254 at the proximal end 250a of the annular member 250 and a second ring 256 at the distal end 250b of the annular member 250. The first ring 254 includes a pair of electrical contacts 258 electrically coupled to the switch 230 via wires 234, the wires 234 extending to the electrical assembly 220 (FIG. 3B) to electrically couple the switch 230 with the circuit board 224 of the adapter assembly 200. The electrical contacts 258 are configured to engage corresponding electrical contacts 356 (FIG. 4F) of the end effector 300, such that the switch 240 and the annular member 250 are capable of transferring data pertaining to the end effector 300 therebetween, ultimately for communication with the power-pack 120, as described in further detail below.

Referring now to FIG. 4A, the end effector 300 is in the form of a single use loading unit. It should be understood, however, that other types of end effectors may also be used with the surgical device 10 of the present disclosure including, for example, end-to-end anastomosis loading units, multi-use loading units, transverse loading units, and curved loading units. As discussed below, the particular end effector 300 utilized with the surgical device 10 is recognized by the power-pack 120 (FIG. 2A) of the handle assembly 100 to enable appropriate operation thereof.

The end effector 300 includes a proximal body portion 310 and a tool assembly 320. The proximal body portion 310 is releasably attachable to the distal cap 206 (FIG. 3A) of the adapter assembly 200 and the tool assembly 320 is pivotally attached to the proximal body portion 310. The tool assembly 320 includes an anvil assembly 330 and a cartridge assembly 340. The anvil and cartridge assemblies 330, 340 are pivotal with respect to each other such that the tool assembly 320 is movable between an open or unclamped position and a closed or clamped position.

Figure 4C:
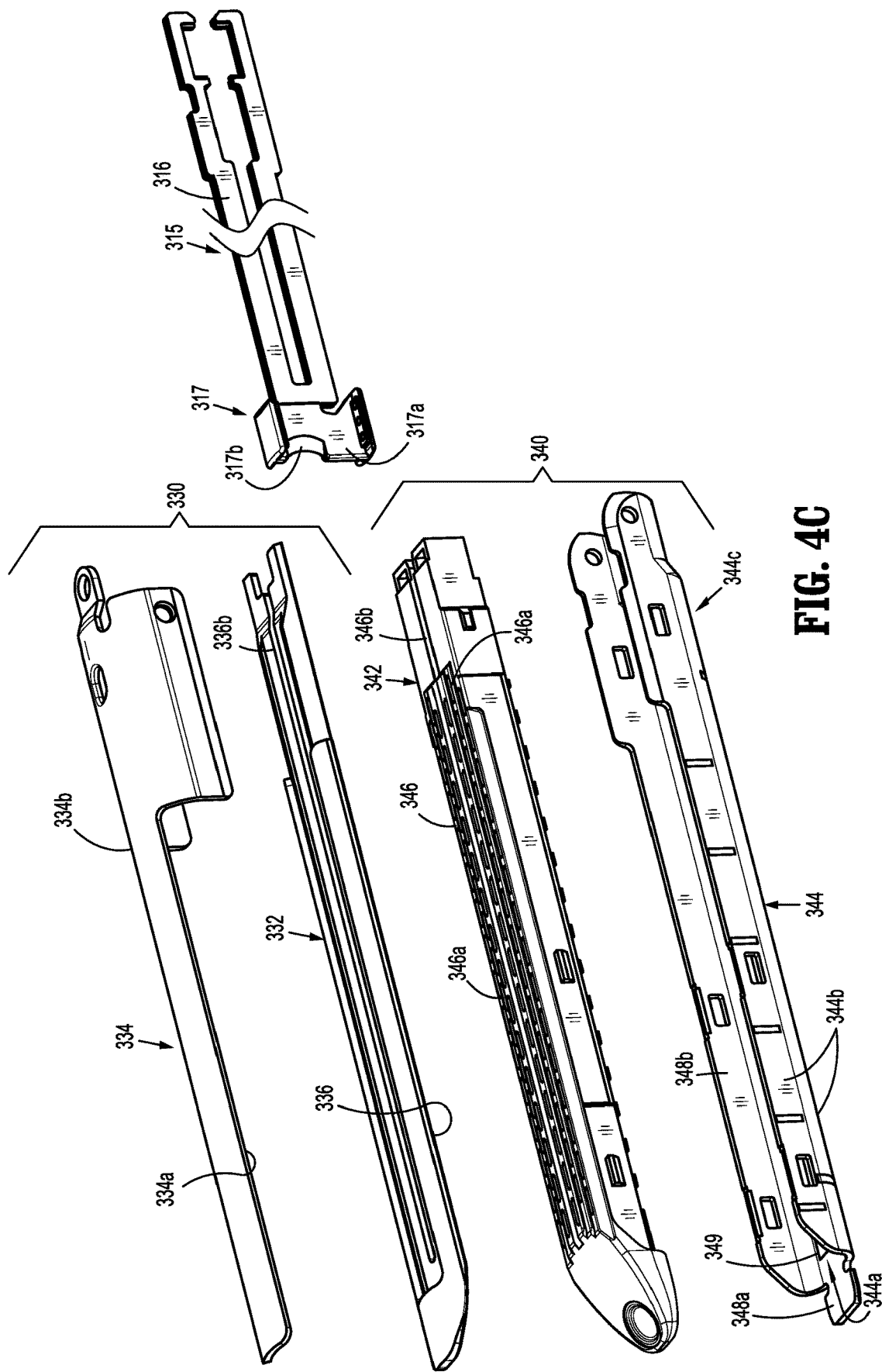
FIG. 4C is a perspective view, with parts separated, of the end effector of the surgical device of FIG. 4A.

As shown in FIGS. 4A-4C, the anvil assembly 330 includes an anvil plate 332 and a cover plate 334 having an inner surface 334a secured over the anvil plate 332 such that the cover plate 334 defines an outer surface 334b of the anvil assembly 330. The anvil plate 332 includes a tissue contacting surface 336 including a plurality of staple forming pockets 336a and a longitudinal slot 336b defined therein.

The cartridge assembly 340 includes a staple cartridge 342 and a cartridge carrier 344. The cartridge carrier 344 defines an elongated support channel 344a configured and dimensioned to selectively receive the staple cartridge 342 therein such that the cartridge carrier 344 defines an outer surface 344b of the cartridge assembly 340. The staple cartridge 342 includes a tissue contacting surface 346 defining staple pockets or retention slots 346a formed therein for receiving a plurality of fasteners or staples (not shown) and a longitudinal slot 346b formed in and extending along a substantial length of the staple cartridge 342.

The proximal body portion 310 of the end effector 300 includes a drive assembly 315 operably associated with and slidably disposable between the anvil and cartridge assemblies 330, 340 for driving the ejection of staples (not shown) from the cartridge assembly 340 of the tool assembly 320, and an articulation link (not shown) for effectuating an articulation of the tool assembly 320. The drive assembly 315 includes an elongated drive beam 316 and an I-beam 317 having a central wall portion 317a including a knife 317b. The knife 317b can travel through the longitudinal slots 336b, 346b defined in the tissue contacting surfaces 336, 346 of the anvil and cartridge assemblies 330, 340, between the staple forming pockets 336a and the retention slots 346a also defined in the respective tissue contacting surfaces 336, 346 to longitudinally cut stapled tissue that is grasped between the tissue contacting surfaces 336, 346 of the anvil and cartridge assemblies 330, 340.

As shown in FIGS. 4C and 4D, the elongated support channel 344a of the cartridge carrier 344 is defined by an inner first or bottom surface 348a and inner second or side surfaces 348b. The inner bottom surface 348a includes a recess 349 defined therein having a first portion 349a that extends longitudinally along a majority of the length of the cartridge carrier 344, and a second portion 349b disposed within a proximal portion 344c of the cartridge carrier 344 that extends at an angular relationship relative to the first portion 349a (e.g., substantially orthogonal thereto) and open to one of the inner side surfaces 348b of the cartridge carrier 344. As shown in FIGS. 4D and 4E, the recess 349 is configured to receive a flex circuit or cable 400 and a strain gauge 450 therein. It is envisioned that the recess 349 may have other configurations that are complementary with the size and shape of a flex cable and/or a strain gauge positioned therein.

As shown in FIG. 4E, the strain gauge 450 is positioned within the first portion 349a of the recess 349 and secured thereto, for example, with an adhesive. The flex circuit 400 is electrically coupled to the strain gauge 450 and extends proximally through part of the first portion 349a of the recess 349, through the second portion 349b of the recess 349, along the inner side surface 348b of the cartridge carrier 344, and proximally along an inner wall (not shown) of the proximal portion 310 (FIG. 4A) of the end effector 300. The flex circuit 400 is secured within the recess 349, the inner side surface 348b of the cartridge carrier 344, and/or to the inner wall of the proximal portion 310 of the end effector 300, for example, with an adhesive. The flex circuit 400 is flexible so that it may bend, curve, or otherwise fit the contours within the end effector 300 to help route signals through the tight/limited space available within the end effector 300.

Figure 4F:
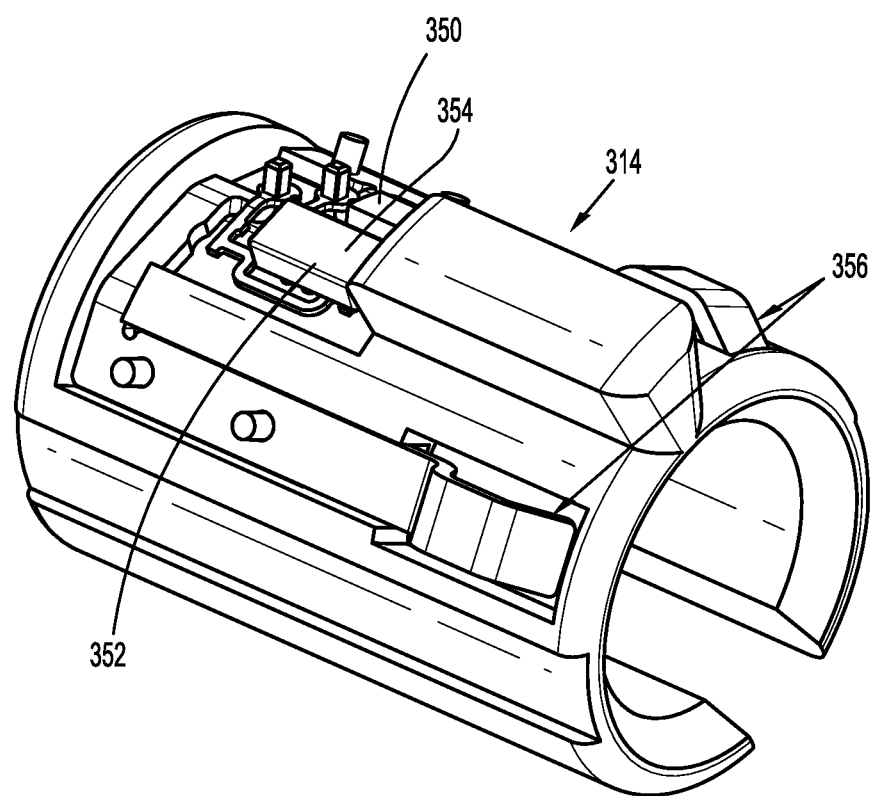
FIG. 4F is a perspective view of an inner housing of the end effector of FIG. 4A.

With reference now to FIG. 4F, in conjunction with FIG. 4A, the end effector 300 further includes an outer housing 312 and an inner housing 314 disposed within the outer housing 312. A proximal end of the outer housing 312 is sized and dimensioned to be inserted through the distal cap 206 (FIG. 3A) of the adapter assembly 200 to engage the adapter assembly 200.

The end effector 300 includes a microcontroller 350 and a memory 352, each of which is disposed within or on the inner housing 314. The microcontroller 350 is electrically coupled to the strain gauge 450 via the flex circuit 400. The microcontroller 350 is configured to receive and/or measure sensor data (e.g., electrical signals) from the strain gauge 450 and record them in the memory 352. The memory 352 includes a memory chip 354 and a pair of electrical contacts 356 electrically connected to the memory chip 354. The memory 352 is configured to store the sensor data received from the microcontroller 250. The sensor data may include, for example, stress measurements along the cartridge assembly 340 which, in turn, may be converted, via an algorithm, into corresponding tissue stress measurements of the tissue disposed between the anvil and cartridge assemblies 330, 340 of the end effector 300.

The memory chip 354 is also configured to store one or more parameters related to the end effector 300. The parameters include, for example, a serial number of a loading unit, a type of loading unit, a size of loading unit, a staple size, information identifying whether the loading unit has been fired, a length of a loading unit, maximum number of uses of a loading unit, and combinations thereof. The memory chip 354 is configured to communicate to the handle assembly 100 the sensor data and/or parameters of the end effector 300, as described above, via the electrical contacts 356, upon engagement of the end effector 300 with the adapter assembly 200, as described below. The sensor data and/or parameters may be processed in the controller circuit board 126 of the handle assembly 100, or in some other remote processor or the like.

The electrical contacts 356 are disposed on an outer surface of the inner housing 314 and are configured to engage the electrical contacts 258 (FIG. 3D) of the annular member 250 of the adapter assembly 200 upon insertion of the end effector 300 into the adapter assembly 200. This connection between the electrical contacts 356 of the end effector 300 and the electrical contacts 258 of the adapter assembly 200 allows for communication between the memory chip 354 of the end effector 300 and the controller circuit board 126 (FIG. 2A) of the power-pack 120 of the handle assembly 100.

With reference now to FIGS. 5A and 5B, the flex circuit 400 includes a body or substrate 410 suitable for supporting and/or electrically connecting electronic components thereto. The electronic components may be, for example, surface mount technology and/or through-hole technology, including, for example, integrated circuits (e.g., microchips, microcontrollers, microprocessors), resistors, amplifiers, inductors, capacitors, sensing elements (e.g., optical sensors, pressure sensors, capacitive sensors), buttons, switches, circuit boards, electrical connectors, cables, and/or wires, among other elements or circuitry within the purview of those skilled in the art. As discussed above, the flex cable 400 electrically interconnects the microcontroller 350 (FIG. 4F) and the strain gauge 450.

The substrate 410 is formed from one or more layers or sheets of dielectric material 420 (also referred to herein as dielectric layer(s)) and one or more layers of conductive material 430 (also referred to herein as conductive layer(s)) that form conductive traces 432 in the substrate 410. The dielectric layers 420 may be formed from polymers such as, for example, polyimides, acrylics, or polyesters, among other flexible and temperature resistant or electrically insulative materials within the purview of those skilled in the art. The conductive layers 430 may be formed from metals such as, for example, copper, gold, nickel, or aluminum, among other materials within the purview of those skilled in the art having low resistivity and that can route signals between electronic components of the flex circuit 400, such as between the strain gauge 450 and the microcontroller 350 (FIG. 4F). Vias (not shown) may be used to interconnect conductive traces 432 through different layers of the flex circuit 400.

The dielectric and conductive layers 420, 430 of the substrate 410 may be joined to one another by, for example, laminating, welding, and/or using adhesives, among other methods and materials within the purview of those skilled in the art. While the flex circuit 400 is shown as a single sided flex circuit, it should be understood that the substrate 410 may be configured to allow for the fabrication of single or double sided flex circuits, multilayer flex circuits, or rigid flex circuits.

Electrical contact regions 434 are disposed at terminal ends of the conductive traces 432 defined through the substrate 410 on a first side 400*a* of the flex circuit 400. Each of the electrical contact regions 434 includes one or more conductive contact points (e.g., solder pads, conductive adhesive, etc.) to which electrical components are attached or otherwise coupled to the substrate 410. The substrate 410 includes a first electrical contact region 434*a* disposed at a first or distal end 410*a* of the substrate 410 which is aligned and soldered to the strain gauge 450, and a second electrical contact region 434*b* disposed at a second or proximal end 410*b* of the substrate 410 to be electrically coupled to the microcontroller 350 (FIG. 4F). It should be understood that while the flex circuit 400 is shown including two electrical contact regions 434*a*, 434*b*, the flex circuit may have any number of electrical contact regions depending upon the desired configuration and functionality of the flex circuit, as is within the purview of those skilled in the art.

The strain gauge 450 includes a polymeric carrier 460 (e.g., one or more layers of dielectric material) and one or more layers of resistive material 470 (also referred to herein as resistive layer(s)) that are patterned to form resistor traces 472 within the polymeric carrier 460. The resistive layers 470 may be formed from metal alloys such as, for example, constantan, which is a copper nickel alloy that exhibits changes in resistance when exposed to strain and relatively minimal changes in resistance as a function of temperature, among other materials within the purview of those skilled in the art having high resistivity, a negative thermal coefficient of resistance, and/or good mechanical properties for measuring strain.

The resistor traces 472 form or are coupled to a resistance bridge, such as a Wheatstone bridge (e.g., a quarter bridge, a half bridge, a full bridge), that can read a strain response of the structure to which the strain gauge 450 is attached. With reference again to FIG. 4E, the strain gauge 450 is positioned within the first portion 349*a* of the recess 349 of the cartridge carrier 344 and is configured to measure deformation of the cartridge carrier 344 due to forces exerted on the cartridge assembly 340 (FIG. 4A) under a loading condition such as, for example, during clamping of tissue within the tool assembly 320 and/or during firing of the end effector 300. The strain experienced by the cartridge carrier 344 is directly transferred to the strain gauge 450 which responds with a change in resistance, the flex circuit 400 providing the excitation voltage to the strain gauge 450 and the return path for sensor data (e.g., voltage readings).

Figures 6A, 6B:
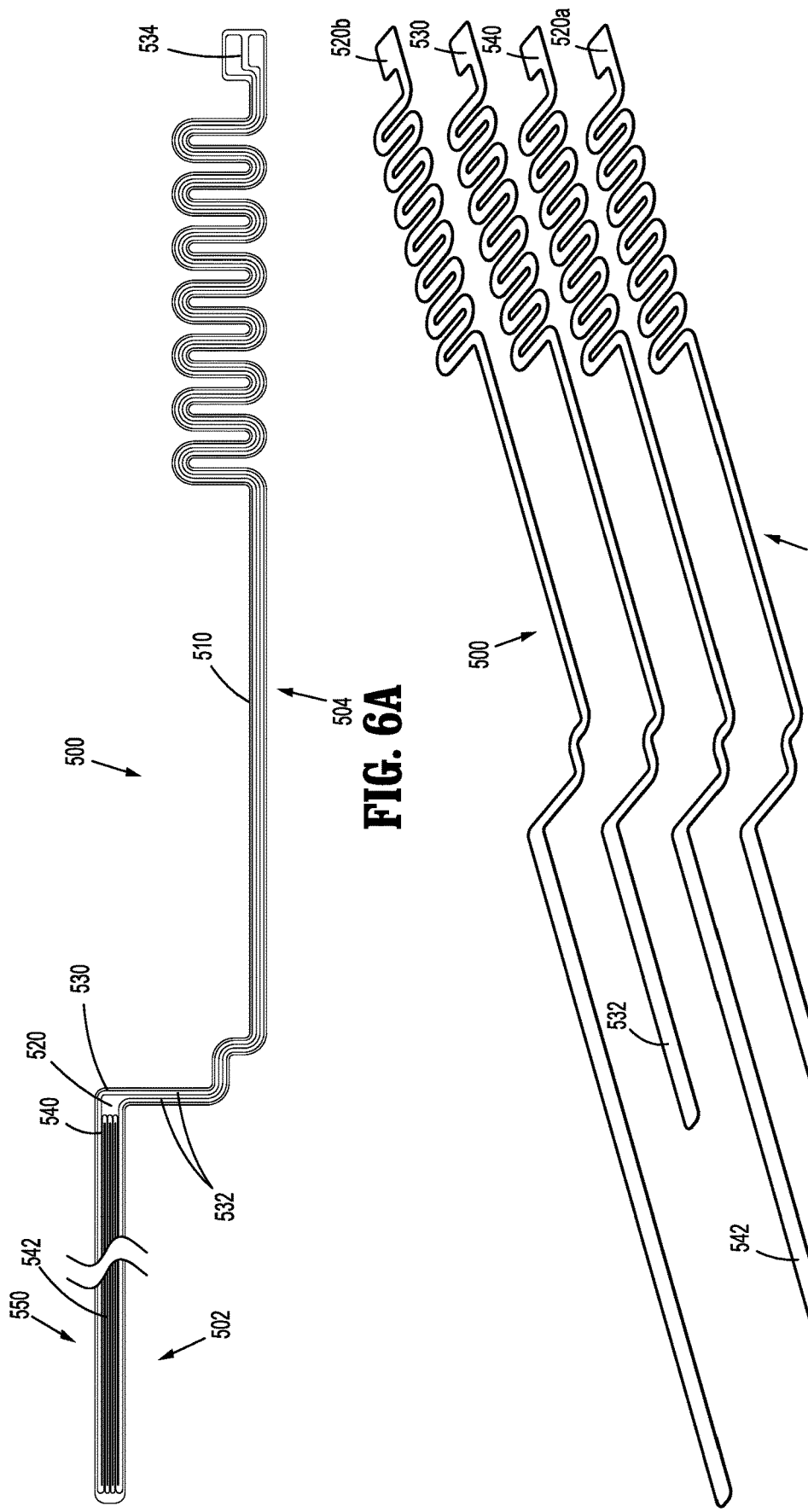
FIG. 6A is a top view of a flex circuit and a strain gauge in accordance with another embodiment of the present disclosure.
FIG. 6B is a perspective view, with parts separated, of the flex circuit of FIG. 6A, showing layers of the flex circuit in accordance with an embodiment of the present disclosure.

With reference now to FIG. 6A, a flex circuit 500 includes a strain gauge 550 embedded therein. The integration of the strain gauge 550 into the flex circuit 500 removes the need for a solder connection or wire bond between the strain gauge 550 and the flex circuit 500 thereby minimizing the spaced needed in the cartridge carrier 344 (FIG. 4E) to get signal and power to the strain gauge 550, reducing potential failure of attachment between the flex circuit 500 and the strain gauge 550, and/or simplifying the assembly process.

The flex circuit 500 includes a substrate 510 including one or more dielectric layers 520, one or more conductive layers 530, and one or more resistive layers 540. Resistor traces 542 are formed in a first region 502 of the flex circuit 500 which corresponds with the first portion 349*a* (FIG. 4D) of the recess 349 of the cartridge carrier 344. The first region 502 of the flex circuit 500 forms the strain gauge 550 such that compression and/or extension of the cartridge carrier 344 changes the length or deforms the resistive layer(s) 540 on the flex circuit 500. As discussed above, using a resistance bridge, such as a Wheatstone bridge, the changes in the resistance are measured. Conductive traces 532 are formed in a second region 504 of the flex circuit 500 to provide a signal path to and from the first region 502 of the flex circuit 500 such as, for example, to and from the microcontroller 350 (FIG. 4F) coupled to the second region 504 of the flex circuit 500 at electrical contact region 534.

With reference now to FIG. 6B, the flex circuit 500 is formed by placing a resistive layer 540 onto a first dielectric layer 520*a*. The resistive layer 540 may extend through both first and second regions 502, 504 of the flex circuit 500 (e.g., the resistive layer may extend the entire length of the flex circuit). The resistive layer 540 in the first region 502 of the flex circuit 500 is patterned to form the resistor traces 542, and the resistive layer 540 in the second region 504 of the flex circuit 500 is a continuous plane of material. The first region 502 is then masked and a conductive layer 530 is placed over the resistive layer 540. The conductive layer 530 is patterned to form the conductive traces 532 in the flex circuit 500. A second dielectric layer 520*b* is then placed over the conductive layer 530. As the conductive and resistive layers 530, 540 are disposed adjacent to and in contact with each other, and the resistive layer 540 has a higher resistance than the conductive layer 530, current will only flow through the conductive layer 530 and the resistive layer 540 changes in resistance as the flex circuit 500 deforms.

In operation of the surgical device 10, upon initial insertion of the end effector 300 into the adapter assembly 200, the switch actuator 240 remains disengaged from the switch 230. With the switch 230 in the unactuated state, there is no electrical connection established between the memory 352 of the end effector 300 and the controller circuit board 126 of the handle assembly 100. Upon a rotation of the end effector 300, the end effector 300 engages the adapter assembly 200 and moves the switch actuator 240 distally, which toggles the switch 230 to actuate the switch 230. With the switch 230 in the actuated state, an electrical connection is established between the memory chip 354 of the end effector 300 and the controller circuit board 126 of the handle assembly 100, through which information about the end effector 300 is communicated to the controller circuit board 126 of the handle assembly 100. Upon both the actuation of the switch 230 and the establishment of a wiping contact between the electrical contacts 356 of the inner housing 314 of the end effector 300 and the electrical contacts 258 of the annular member 250 of the adapter assembly 200, the handle assembly 100 is able to detect that the end effector 300 is engaged with the adapter assembly 200 and to identify one or more parameters of the end effector 300 and/or to process the sensor data from the strain gauge 450, 550 of the end effector 300. Accordingly, the power-pack 120 is capable of reading the information stored in the memory 352 of the end effector 300 via the adapter assembly 200.

With the end effector 300 engaged to the adapter assembly 200, the strain gauge 450, 550 of the end effector 300 detects and/or measures mechanical behaviors and/or properties of the tool assembly 320 in real time during a surgical procedure. The sensor data is transmitted to the microcontroller 350 via the flex circuit 400, 500 for processing, stored in the memory 352, and ultimately transferred to the power-pack 120 of the handle assembly 100 via the adapter assembly 200 along the 1-wire bus, or other communication protocol. The power-pack 120 collects and processes the sensor data in real time, and transmits electrical control signals to the motors 128*a*, 128*b*, 128*c* of the handle assembly 100 to control a function of the surgical device (e.g., to change an operating parameter, such as pre-compression time, speed of firing, etc.). The mechanical behaviors and/or properties of the tool assembly 320 detected/measured by the strain gauge 450, 550 are then converted and/or correlated to real time, or near real time, behaviors and/or properties of the target tissue clamped in the tool assembly 320.

For example, in a method of using the surgical device 10 of the present disclosure, the end effector 300 is placed at a desired surgical site and the anvil assembly 330 and the cartridge assembly 340 are approximated and clamped to grasp target tissue between the respective tissue contacting surfaces 336, 346 of the anvil and cartridge assemblies 330, 340. The strain gauge 450, 550 measures stress in the cartridge assembly 340, and in turn, measures stress in the target tissue. Specifically, the resistance of the strain gauge 450, 550 is sent to the microcontroller 350 of the end effector 300 which, in turn, processes the resistance to calculate a force or pressure on the strain gauge 450, 550 which, ultimately, is transmitted to the power-pack 120 of the handle assembly 100 via the adapter assembly 200. The power-pack 120 processes the sensor data and controls the wait time between clamping of the target tissue and firing of staples from the cartridge assembly 340 until a stress on the target tissue is at a value within an acceptable range of values. Accordingly, the microcontroller 350 may continuously or intermittently monitor the strain gauge 450, 550 for collection of the sensor data. The handle assembly 100 may provide a visual or audible indication to a user that the surgical device 10 is ready for firing. The wait time is beneficial to minimize or avoid negative acute events related to excess stress in the target tissue, such as bruising, tearing, and bleeding. The strain gauge 450, 550 controls the firing of the surgical device 10 to keep the target tissue stress within an ideal stress region which is beneficial for sealing the target tissue, allowing perfusion for healing, providing hemostasis and pneumostasis, and/or preventing leakage.

It should be understood that various modifications may be made to the embodiments of the presently disclosed surgical device. For example, the end effector of the present disclosure may be modified to additionally or alternatively include a strain gauge/flex circuit in the anvil assembly. As another example, it should be understood that the handle assembly, the adapter assembly, and/or the end effector may be modified depending on the desired use of the surgical device of the present disclosure. For example, handle assemblies, end effectors and/or adapter assemblies of the present disclosure may be configured to perform, for example, endoscopic gastro-intestinal anastomosis (EGIA) procedures or end-to-end anastomosis (EEA) procedures. For a detailed description of the structure and function of exemplary handle assemblies, adapter assemblies, and end effectors, reference may be made to commonly owned U.S. Patent Publication No. 2016/0296234 ("the '234 Publication"), the entire content of which is incorporated herein by reference, and the '134 Publication, the entire content of which was previously incorporated herein by reference. Therefore, the above description should not be construed as limiting, but merely as exemplifications of embodiments. Those skilled in the art will envision other modifications within the scope and spirit of the present disclosure.

What is claimed is:

1. A surgical device, comprising:
an end effector including a proximal body portion and a tool assembly pivotally connected to the proximal body portion, the tool assembly including:
an anvil assembly;
a cartridge carrier pivotally connected to the anvil assembly, the cartridge carrier including:
a first wall defining an inner first surface;
a pair of second walls extending from the first wall in spaced relation relative to each other and defining inner second surfaces, wherein the inner first surface of the first wall and the inner second surfaces of the pair of second walls define an elongated support channel; and
a strain gauge disposed within the elongated support channel and supported on the inner first surface of the first wall; and
a flex cable including:
a distal portion disposed within the elongated support channel and supported on the inner first surface of the first wall, the distal portion of the flex cable being electrically coupled to the strain gauge, the distal portion of the flex cable having a first profile; and
a proximal portion disposed at least partially within the elongated support channel and supported on the inner second surface of one of the pair of second walls and disposed at least partially within the proximal body portion of the end effector, the proximal portion of the flex cable having a second profile that is perpendicular to the first profile.

2. The surgical device according to claim 1, wherein the cartridge carrier includes a recess defined within the inner first surface of the first wall and being in open communication with the elongated support channel, wherein the strain gauge is disposed within the recess defined within the inner first surface.

3. The surgical device according to claim 2, wherein the distal portion of the flex cable is disposed within the recess defined within the inner first surface.

4. The surgical device according to claim 3, wherein the recess defined within the inner first surface includes:
a first portion extending longitudinally along a majority of the length of the cartridge carrier; and
a second portion disposed at an angular orientation relative to the first portion, the second portion being orthogonal to the first portion such that the first portion and second portion of the recess define an L-shape, the second portion having:
a first end in open communication with a proximal end of the first portion; and
a second end in open communication with one of the inner second surfaces of the pair of second walls, the second portion of the recess being defined partially within the one of the inner second surfaces of the cartridge carrier.

5. The surgical device according to claim 4, wherein the second end of the second portion of the recess is defined partially within the one of the inner second surfaces of the cartridge carrier.

6. The surgical device according to claim 5, wherein the distal portion of the flex cable has a first segment disposed within the first portion of the recess, a second segment orthogonal to the first segment and disposed within the second portion of the recess, and the proximal portion of the flex cable includes a first segment orthogonal to the second segment of the distal portion and parallel to the first segment of the distal portion.

7. The surgical device according to claim 1, wherein the proximal portion of the flex cable extends proximally beyond the cartridge carrier.

8. The surgical device according to claim 7, wherein the proximal portion of the flex cable extends along an inner wall of the proximal body portion.

9. The surgical device according to claim 1, wherein the strain gauge is embedded within the flex cable.

10. The surgical device according to claim 1, wherein the end effector further includes a microcontroller coupled to a memory, the microcontroller electrically coupled to the strain gauge and configured to receive sensor data from the strain gauge, the memory configured to store the sensor data.

11. The surgical device according to claim 1, further comprising a handle assembly operably coupled to the end effector, the handle assembly including a power-pack configured to receive sensor data from the strain gauge of the end effector and to control a function of the end effector in response to the sensor data.

12. The surgical device according to claim 1, further comprising a staple cartridge disposed within the elongated support channel of the cartridge carrier.

13. A surgical device, comprising:
a staple cartridge configured to fire surgical staples;
an end effector including a proximal body portion and a tool assembly pivotally connected to the proximal body portion, the tool assembly including:
an anvil assembly;
a cartridge carrier configured to selectively receive the staple cartridge, the cartridge carrier being pivotally connected to the anvil assembly, the cartridge carrier including:
a first wall defining an inner first surface;
a pair of second walls extending from the first wall in spaced relation relative to each other and defining inner second surfaces, wherein the inner first surface of the first wall and the inner second surfaces of the pair of second walls define an elongated support channel; and
a strain gauge disposed within the elongated support channel and supported on the inner first surface of the first wall; and
a flex cable including:
a distal portion disposed within the elongated support channel and supported on the inner first surface of the first wall, the distal portion of the flex cable being electrically coupled to the strain gauge, the distal portion of the flex cable having a first profile; and
a proximal portion disposed at least partially within the elongated support channel and supported on the inner second surface of one of the pair of second walls and disposed at least partially within the proximal body portion of the end effector, the proximal portion of the flex cable having a second profile that is perpendicular to the first profile; and
a handle assembly operably supporting the end effector, the handle assembly including a power-pack configured to receive sensor data from the strain gauge of the end effector and to control a firing of the staple cartridge in response to the sensor data.

14. The surgical device according to claim 13, wherein the cartridge carrier includes a recess defined within the inner first surface of the first wall and being in open communication with the elongated support channel, wherein the strain gauge is disposed within the recess defined within the inner first surface.

15. The surgical device according to claim 14, wherein the distal portion of the flex cable is disposed within the recess defined within the inner first surface.

16. The surgical device according to claim 15, wherein the recess defined within the inner first surface includes:
- a first portion extending longitudinally along a majority of the length of the cartridge carrier; and
- a second portion disposed at an angular orientation relative to the first portion, the second portion being orthogonal to the first portion such that the first portion and second portion of the recess define an L-shape, the second portion having:
  - a first end in open communication with a proximal end of the first portion; and
  - a second end in open communication with one of the inner second surfaces of the pair of second walls, the second portion of the recess being defined partially within the one of the inner second surfaces of the cartridge carrier.

17. The surgical device according to claim 16, wherein the second end of the second portion of the recess is defined partially within the one of the inner second surfaces of the cartridge carrier.

18. The surgical device according to claim 17, wherein the distal portion of the flex cable has a first segment disposed within the first portion of the recess, a second segment orthogonal to the first segment and disposed within the second portion of the recess, and the proximal portion of the flex cable includes a first segment orthogonal to the second segment of the distal portion and parallel to the first segment of the distal portion.

19. The surgical device according to claim 13, wherein the end effector further includes a microcontroller coupled to a memory, the microcontroller electrically coupled to the strain gauge and configured to receive sensor data from the strain gauge, the memory configured to the sensor data.

20. The surgical device according to claim 13, wherein the handle assembly further includes a microcontroller coupled to a memory, the microcontroller electrically coupled to the strain gauge and configured to receive sensor data from the strain gauge, the memory configured to store the sensor data.

* * * * *